United States Patent [19]
Reuter et al.

[11] Patent Number: 4,771,077
[45] Date of Patent: * Sep. 13, 1988

[54] SPRAY DRIED ACETAMINOPHEN

[75] Inventors: Gerald L. Reuter, Plattsburgh, N.Y.; Robert G. Blank, Vineland, N.J.

[73] Assignee: American Home Products Corporation (Del.), New York, N.Y.

[*] Notice: The portion of the term of this patent subsequent to Jul. 26, 2005 has been disclaimed.

[21] Appl. No.: 921,558

[22] Filed: Oct. 21, 1986

[51] Int. Cl.⁴ .......................................... A61K 31/74
[52] U.S. Cl. .................................. 514/629; 424/495; 424/78
[58] Field of Search ................. 424/78, 495; 514/629

[56] References Cited

U.S. PATENT DOCUMENTS 4,013,785  3/1977  Weintraub et al. ................. 514/629

FOREIGN PATENT DOCUMENTS 58-172311  10/1983  Japan .

OTHER PUBLICATIONS

Chem. Abstracts vol. 92, entry 135303w.

Primary Examiner—Joseph L. Schofer
Assistant Examiner—Peter F. Kulkosky
Attorney, Agent, or Firm—John W. Routh

[57] ABSTRACT

A therapeutic taste-neutral powder form of acetaminophen obtained by spray-drying a suspension of colloidal silica in a lower alkanol solution of acetaminophen and ethyl cellulose.

6 Claims, No Drawings

SPRAY DRIED ACETAMINOPHEN

BACKGROUND OF THE INVENTION (a) Field of the Invention

This invention relates to a novel therapeutic form of spray dried acetaminophen having a neutral taste which can be formulated into, for example chewable tablets and fast dissolving dosage forms as described in U.S. Pat. Nos. 4,305,502 and 4,371,516. More specifically this invention relates to a taste-neutral spray dried powder formed by spray drying a solution of acetaminophen and ethylcellulose in a lower alkanol having suspended therein colloidal silica. By taste-neutral it is meant that the powder has essentially no taste and is neither sweet nor bitter.

(b) Prior Art

Acetaminophen, a widely used analgesic and antipyretic, is not palatable enough to be used in chew-type tablets for those people who do not swallow whole solid-type dosage forms.

The use of flavor agents e.g. chocolate, banana, orange, lemon, licorice, root beer, and raspberry, in particular, have been proposed for bitter tasting drugs. These agents are not dependable masking ingredients. Mint flavors can be useful in ameliorating a chalky taste parameter. Bitter properties, however, are very difficult to mask to any great extent, particularly, when they do not mimic the expected natural taste of the flavor agent.

Other properties including mouthfeel also need to be addressed in consideration of the oral acceptance of chewable or chew-type tablets.

The fast dissolving dosage forms described in U.S. Pat. Nos. 4,305,502 and 4,371,516 are manufactured to disintegrate in water within five seconds or less and hence dissolve rapidly in the saliva of the mouth. Heretofore the use of such dosage forms was restricted to pharmaceuticals which had a neutral taste or a slightly disagreeable taste which could be masked by a flavoring agent. Pharmaceuticals with a bitter taste such as acetaminophen and ibuprofen, however, could not heretofore be used in such dosage forms.

SUMMARY OF THE INVENTION

According to this invention, a novel therapeutic taste-neutral powder form of spray-dried acetaminophen is provided which can be formulated into chewable tablets and the like. The powder is formed by spray drying a solution of acetaminophen and ethyl cellulose in a lower alkanol having colloidal silica suspended therein. Preferably the lower alkanol is ethanol.

According to another aspect of this invention, a pharmaceutical dosage for oral administration as a solid is provided, which dosage form can be disintegrated by water at 37° C. within ten seconds, and comprises as the pharmaceutical agent incorporated therein the taste neutral powder form of spray dried acetaminophen of the invention.

DETAILS OF THE INVENTION

The acetaminophen useful in this inveniton is the pharmaceutical grade. The ethyl cellulose useful in this invention is also National Formulary or pharmaceutical grade. Suitable grades are the ETHOCEL brand marketed by Dow Chemical Company, Midland, Mich. and that marketed by Hercules, Inc. of Wilmington, Del.

The colloidal silica useful in this invention has a particle size of about 10 millimicrons. Suitable grades are Cabosil-M-5 marketed by Cabot Corporation of Boston, Mass., and that sold by PQ Company, Philadelphia, Pa.

The weight percent of acetaminophen in the taste neutral powder can be from about 40 to 70% by weight and the weight percent of the ethylcellulose can range from 15% to 30% by weight. At 15% by weight of ethylcellulose, there may be slightly bitter taste but at 20% and above the powder is taste neutral. The weight percent of colloidal silica in the taste neutral powder can be from about 15% to 30% by weight.

The solvent for the ethylcellulose can be one of the alkanols such as methyl, ethyl, isopropyl or mixtures thereof, but must be an organic solvent in which the acetaminophen is soluble.

A small amount of a hydrophobic substance such as castor oil can be added to the solution to inhibit leaching of the acetaminophen from the spray dried powder. A small amount of glyceryl monostearate can be added to improve taste masking.

Spray dryers can be of the usual laboratory or commercial type. Suitable spray dryers are manufactured by Buchi Laboratoriums-Technik AG by the Anhydro Company of Attleboro, Mass. and Niro Atomizer Inc., of Columbia, Md.

The spray dryer employed in the following examples was a Buchi 190 Mini Spray Dryer. The operating conditions for the Bucci Mini Spray Drier are customarily an inlet temperature of 220° C. and an outlet temperature of 130° C.

The following examples illustrate the formation of the taste-neutral spray dried acetaminophen powder of the invention. In these examples, the ethyl cellulose was obtained from Hercules Chemical Company, Wilmington Del. It was a dry material of the standard type having a viscosity designation of 10 and an ethoxy content of 48.0% to 49.5%.

EXAMPLE I

In this example, the feed mixture to the spray dryer was composed of the following materials.

| Ingredient | Weight % Solids in Suspension | Weight % Solids in powder | Grams Ingredient in suspension |
| --- | --- | --- | --- |
| Acetaminophen, USP | 70 | 70 | 85 |
| Ethyl Cellulose, NF | 15 | 15 | 18 |
| Colloidal Silica | 15 | 15 | 18 |
| Ethyl Alcohol | — | — | q.s. 2500 ml. |
| Total: | 100% | 100% | 2600 grams |

The acetaminophen was dissolved in a portion of the alcohol contained in a stainless steel mixing vessel with the aid of a Lightnin mixer. The ethyl cellulose was dissolved in the remaining alcohol is a separate stainless steel mixing vessel and the contents of the two mixing vessels were filtered and combined. The colloidal silica was added and mixed until a homogeneous dispersion was obtained. The dispersion was then transferred to the feed hopper of the Buchi Mini Spray Dryer.

The spray drier was operated such that an air inlet temperature of 220°–225° C. and an air outlet temperature of 150°–155° C. was maintained throughout the run.

The yield of spray dried powder was about 90% of theoretical. The product was a white, fine powder having a particle size such that 95% was between 2 and 50 microns.

The freshly obtained product upon tasting produced no bitterness characteristic of acetaminophen. Upon aging one month at room temperature the product remained quite acceptable without bitterness.

EXAMPLE 2

In this example, the amounts of the ingredients were changed as follows:

| Ingredient | Weight % Solids in Suspension | Weight % solids in powder | Grams Ingredient in suspension |
|---|---|---|---|
| Acetaminophen, USP | 70 | 70 | 70 |
| Ethyl Cellulose, NF | 15 | 15 | 15 |
| Colloidal Silica | 15 | 15 | 15 |
| Ethyl Alcohol | — | — | q.s. 1500 ml. |
| Total | 100% | 100% | ≈1600 grams |

The spray dryer was operated such that an air inlet temperautre of 220° C.–225° C. and an air outlet temperature of 150° C. to 155° C. was maintained throughout the run.

EXAMPLE 3

In this example, the amounts of the ingredients were changed as follows:

| Ingredient | Weight % Solids in Suspension | Weight % solids in powder | Grams Ingredient in suspension |
|---|---|---|---|
| Acetaminophen, USP | 40 | 40 | 40 |
| Ethyl Cellulose, NF | 30 | 30 | 30 |
| Colloidal Silica | 30 | 30 | 30 |
| Ethyl Alcohol | — | — | q.s. 2500 ml. |
| Total | 100% | 100% | ≈2600 grams |

The spray dryer was operated such that an air inlet temperature of 220° C.–226° C. and an air outlet temperature of 150° C. to 155° C. was maintained throughout the run.

The product from the spray drier, when tasted, produced no bitterness.

EXAMPLE 4

In this example, isopropyl alcohol was used instead of ethyl alcohol and the feed mixture to the spray dryer was composed of the following materials.

| Ingredient | Weight % Solids in powder | Grams Ingredient per 500 ml of suspension |
|---|---|---|
| Acetaminophen, USP | 70 | 23.33 |
| Isopropyl Alcohol | — | 200.00 |
| Ethyl Cellulose, NF | 15 | 5.00 |
| Colloidal Silica | 15 | 5.00 |
| Isopropyl Alcohol | — | q.s. 500 ml. |
| Total: | 100% | |

The acetaminophen was dissolved in a portion of the alcohol contained in a stainless steel mixing vessel with the aid of a Lightnin mixer. Eighty percent of the acetaminophen dissolved in 30 minutes, ninety percent dissolved after 60 minutes and all was dissolved in 3 hours except for a small residue. The ethyl cellulose was dissolved in a second portion of the alcohol in a separate stainless steel mixing vessel. The ethylcellulose did not dissolve in 2 hours but was left overnight and by morning it was mostly dissolved. After one hour mixing with the Lightnin mixer, it was completely solubilized. The contents of the two mixing vessels were then combined. The colloidal silica was added and mixed until a homogeneous dispersion was obtained. Isopropyl alcohol was then added g.s. to 500 ml. The dispersion was then transferred to the feed tank of the Buchi Mini Spray Dryer.

The spray drier was operated such that an air inlet temperature of 180°–185° C. and an air outlet temperature of 113° C. was maintained throughout the run.

The freshly obtained white powder upon tasting produced a somewhat bitter taste characteristic of acetaminophen.

EXAMPLE 5

In this example, methanol was used instead of ethyl alcohol and the feed mixture to the spray dryer was composed of the following materials.

| Ingredient | Grams Ingredient per 1500 ml suspension |
|---|---|
| Acetaminophen, USP | 210 |
| Ethyl Cellulose, NF | 45 |
| Colloidal Silica | 3 |
| Clycerol Monostearate | 3 |
| Methyl Alcohol | q.s. 1500 ml. |

Methanol in the amount of 780 ml was placed in a stainless steel mixing vessel equipped with a Lightnin mixer and 210 grams of acetaminophen were added. After mixing for one hour, 90% of the acetaminophen had dissolved. Methanol in the amount of 690 ml was placed in another stainless steel mixing vessel equipped with a Lightnin mixer and the speed was adjusted to produce a vortex. The ethyl cellulose (45 grams) was then added and mixing continued for one hour until the ethyl cellulose had dissolved. The contents of the two mixing vessels were combined and methanol added q.s. to 1500 ml. Mixing was continued for one half hour until all solids had dissolved.

Five hundred milliliters of this solution were then transferred to a separate mixing vessel and one gram of colloidal silica was added with mixing until uniform. In order to improve dispersion of the colloidal silica and maintain the other solids in solution, one gram of glyceryl monostereate (Tegin 515) was added. The dispersion was then transferred to the feed tank of the Buchi Portable Spray Dryer.

The spray drier was operated such that an air inlet temperature of 120°–122° C. and an air outlet temperature of 78°–82° C. was maintained throughout the run.

The freshly obtained product upon tasting was very slightly bitter.

The particle size of the product from the spray dryer again was predominantly in the 2 to 50 micron range with 50% the product having a particle size less than 20 microns and no particles greater than 100 microns.

The product freshly obtained from the spray dryer, when tasted, produced a very slight bitterness in the mouth. Particulate perception in the mouth is about about 20 microns so that the powder produced a good mouthfeel.

EXAMPLE 6

This example describes the preparation of fast dissolving dosage forms using the spray dried taste-neutral acetaminophen of Example 1 and other ingredients as follows:

| Ingredients | Weight % suspension | Grams in suspension |
|---|---|---|
| Gelatin, BY 19/50 | 4.0 | 10.00 |
| Mannitol, granular | 3.0 | 7.50 |
| Deionized water | 67.10 | 167.75 |
| NUTRASWEET, NF | 1.20 | 3.00 |
| Cherry #271 | 0.40 | 1.00 |
| Cream Flavor #59.200/A | 0.20 | 0.50 |
| Sodium laurylsulfate | 0.10 | 0.25 |
| Croscarmellose sodium, Type A | 1.00 | 2.50 |
| Powder, Example 1 | 23.0 | 57.50 |

The procedure for preparing a batch of the above suspension takes place in two stages, i.e. the preparation of the gelatin base and the addition of the pharmaceutical agent.

The gelatin base is prepared by adding the gelatin to the deionized water at 30° C. and mixing until the gelatin is dissolved. The solution is then cooled to 25° C. and the mannitol, the sodium lauryl sulfate, the sweetener, and the flavors are separately added and dissolved.

The croscarmellose sodium in powder form (Ac-DiSol) and the taste-neutral spray dried acetaminophen powder are dry mixed and screened through a 20 mesh screen. The mixed powder is added to the gelatin solution and further admixed with a homomixer for thirty minutes to form a uniform dispersion.

The freeze drier employed in this example is a Virtis 25 SRC Model Freeze Drier. The fast dissolving dosage forms are prepared by dosing 500 milligrams of the suspension of acetaminophen into each well in a thermoformed blister tray containing 10 wells per tray. The filled trays are placed in a larger tray containing a dry ice-methanol mixture. When the suspension in the wells are frozen, the samples are placed on the freeze dryer trays at a shelf temperature of −45° C.

When the samples have reached a temperature of −45° C., as determined by a probe in a well, the condenser is turned on the freezer turned off. The condenser temperature is brought to between −40° and −45° C. and the vacuum is turned on to between 50 and 60 millitorrs. The heater is then turned on and the shelf temperature is adjusted to 50°-55° C. The heat-dry cycle lasts for 4 hours. The vacuum, the condenser and the heater are turned off and the samples removed. The wafers from each batch are removed from the wells in the trays. They are white in color and each weighs about 150 milligrams of which about 80 milligrams is acetaminophen. The wafers from each batch when placed on the tongue exhibit a cherry/cream flavor with a very slight bitter after taste. When placed in water at 37° C. the wafers disintegrate in less than ten seconds.

EXAMPLE 7

This example describes the preparation of a chewable tablet using the spray dried taste neutral acetaminophen of Example 2 and other ingredients as follows:

| Ingredients | Weight |
|---|---|
| Powder of Example 2, | 500 mg |
| Aluminum Stearate | 2 mg |
| Sorbitol | q.s. to 700 mg |
| Total | 700 mg |

The powder of Example 2 contained 70% by weight or 350 mg of acetaminophen. The ingredients were mixed in a suitable mixer and formed into tablets. The tablets when chewed in the mouth had a neutral taste and good mouthfeel. The taste could be improved by incorporation into the tablet of suitable flavoring agents such as a mint flavoring agent.

We claim:

1. A therapeutic taste neutral powder form of spray-dried acetaminophen which consists essentially of, based upon the weight of the powder, about 40% to 70% by weight acetaminophen, about 15% to 30% by weight ethyl cellulose and about 15% to 30% by weight colloidal silica, the powder having been spray dried from a suspension of the colloidal silica in a lower alkanol solution of the acetaminophen and ethyl cellulose.

2. In a pharmaceutical dosage form for oral administration as a solid, which dosage form can be disintegrated by water within ten seconds, the improvement which comprises incorporating into such dosage form as the pharmaceutical substance a therapeutic taste-neutral powder form of spray-dried acetaminophen which consists essentially of, based upon the weight of the powder, about 40% to 70% by weight acetaminophen, about 15% to 30% by weight ethyl cellulose and about 15% to 30% by weight colloidal silica, the powder having been spray dried from a suspension of the colloidal silica in a lower alkanol solution of the acetaminophen and ethyl cellulose.

3. The taste neutral powder of claim 1 wherein the lower alkanol is ethyl alcohol.

4. The dosage form of claim 2 wherein the lower alkanol is ethyl alcohol.

5. In a pharmaceutical dosage form for oral administration as a solid chewable taste-newtral tablet containing acetaminophen, the improvement which comprises incorporating into such tablet as the pharmaceutical substance a therapeutic taste-neutral powder form of spray-dried acetaminophen which consists essentially of based upon the weight of the powder, about 40% to 70% by weight acetaminophen, about 15% to 30% by weight ethyl cellulose and about 15% to 30% colloidal silica, the powder having been spray dried from a suspension of the colloidal silica in a lower alkanol solution of the acetaminophen and ethyl cellulose.

6. The dosage form of claim 5 wherein the lower alkanol is ethanol.

* * * * *